(12) United States Patent
Kalra et al.

(10) Patent No.: US 6,720,289 B2
(45) Date of Patent: Apr. 13, 2004

(54) FORMULATION AND METHOD FOR INCREASING THE ESSENTIAL OIL CONTENT IN AROMATIC CROPS

(75) Inventors: Alok Kalra, Uttar Pradesh (IN); Neetu Katiyar, Uttar Pradesh (IN); Sushil Kumar, Uttar Pradesh (IN); Suman Preet Singh Khanuja, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 135 days.

(21) Appl. No.: 10/035,641

(22) Filed: Nov. 9, 2001

(65) Prior Publication Data

US 2003/0089034 A1 May 15, 2003

(51) Int. Cl.$^7$ .................. A01N 43/40; A01N 37/10; A01N 37/40; A01N 37/44
(52) U.S. Cl. .................. 504/260; 504/322; 504/326; 504/337; 504/354
(58) Field of Search ................. 504/322, 337, 504/326, 354, 260

(56) References Cited

U.S. PATENT DOCUMENTS

| | | | | |
|---|---|---|---|---|
| 5,439,873 A | * | 8/1995 | Kinnersley | .......... 504/158 |
| 5,840,656 A | * | 11/1998 | Kinnersley et al. | .......... 504/115 |
| 6,083,877 A | * | 7/2000 | Kinnersley et al. | .......... 504/147 |

OTHER PUBLICATIONS

Zimmerli et al., *Proc. Nat'l Acad. Sci. USA* 97:12920–12925 (2000).
Cohen et al., *Eur. J. Plant Pathol.*, 105:351–61 (1999).
Ram et al., *Journal of Medicinal and Aromatic Plant Sciences*, 19:24–27 (1997).
Pancheva et al., *Journal of Plant Physiology*, 149:57–63 (1996).
Lyon et al., *Plant Pathology*, 44:407–27 (1995).
Krajncic & Nemec, *Journal of Plant Physiology*, 146–754–756 (1995).
Cohen et al., *Plant Physiology*, 104–59–66 (1994).
Berglund et al, *Journal of Plant Physiology*, 141:596–600 (1993).

* cited by examiner

Primary Examiner—S. Mark Clardy
(74) Attorney, Agent, or Firm—Baker Botts LLP

(57) ABSTRACT

The present invention provides a formulation for increasing the synthesis and accumulation of essential oil in aromatic plants and other plants. The formulation disclosed herein comprises a resistance inducer, such as an isomer of amino butyric acid or another amino acid, which is capable of increasing the synthesis of essential oil in an aromatic plant. The formulation may further comprise secondary metabolites as well as a carrier. Aromatic plants that may be used in the present invention include, but are not limited to, rose-scented geranium (*Pelargonium graveolens*) and menthol mint (*Mentha arvensis*). The present invention also provides a method of increasing the essential oil content in aromatic crops and other plants.

15 Claims, No Drawings

FORMULATION AND METHOD FOR INCREASING THE ESSENTIAL OIL CONTENT IN AROMATIC CROPS

FIELD OF THE INVENTION

The present invention relates to a formulation and a method useful for increasing the essential oil content of aromatic crops. In particular, this invention relates to a formulation comprising an amino acid, such as an isomer of amino butyric acid, wherein the formulation is capable of increasing or enhancing the essential oil content in aromatic plants.

BACKGROUND OF THE INVENTION

The concept of inducing resistance in plants in laboratories, glasshouse studies, and in the field has been demonstrated using abiotic and biotic elicitors, which may include complex carbohydrates, various amino and fatty acids, derivatives of salicylic, nicotinic and jasmonic acids, ethylene, glycoproteins, and the like. (Lyon et al., *Plant Pathology*, 44:407–27 (1995)).

Such elicitors have also been shown to induce other biochemical changes, which affect plants and plant cell systems, such as photosynthesis (Pancheva et al., *Journal of Plant Physiology* 149:57–63 (1996)), anthocyanin accumulation (Berglund et al., *Journal of Plant Physiology*, 141:596–600 (1993)) and flowering (Krajncic and Nemec, *Journal of Plant Physiology*, 146:754–756 (1995)). These findings indicate that elicitors act as signal molecules for gene expression in plants. However, compounds or chemicals (such as elicitors) capable of enhancing the yields of secondary metabolites (such as essential oil) in aromatic plants, in vivo, are not presently known in the art.

The essential oil of aromatic plants typically comprises a mixture of various terpenes, which are synthesized as a result of a large amount of enzyme activity in multibranched pathway(s). (Ram et al., *Journal of Medicinal and Aromatic Plant Sciences*, 19:24–27 (1997)). The present application examines how compounds such as the elicitors described above may affect the synthesis of essential oil while altering various biochemical pathways.

Amino butyric acid, a non-protein amino acid, has known biological effects in plants and animals. (Zimmerli et al., *Proc. Nat'l Acad. Sci. USA* 97:12920–12925 (2000)). Isomers of amino butyric acid have been identified as regulatory molecules in physiological processes of plants, for example in inducing resistance against phytopathogenic organisms. Examples of such activity include: inducing resistance against *Peronospora parasitica* in Arabidopsis (Zimmerli et al., *Proc. Nat'l Acad. Sci. USA* 97:12920–12925 (2000)); inducing resistance against *Plasmopara viticola* in grapes. (Cohen et al., *Eur. J. Plant Pathol.*, 105:351–61 (1999)); and inducing resistance against *Phytophthora infestans* in tomatoes. (Cohen et al., *Plant Physiology* 104:59–66 (1994)).

However, the prior art has not examined the role that amino butyric acid may have in enhancing the synthesis and accumulation of essential oil in plants. Thus, the findings of the present invention may be useful in applications and industries such as plant-derived aromas and mediculture. In addition, increasing the essential oil content in aromatic crops may provide for minimizing the use of chemical fungicides.

Therefore, a need exists for a formulation and a method for enhancing or increasing the essential oil content or yields in aromatic crops. More particularly, a need exists to provide a formulation comprising, for example, a non-protein amino acid, such as DL-2 amino butyric acid to increase the synthesis and accumulation of the quantities of essential oil, in vivo, in aromatic plants.

SUMMARY OF THE INVENTION

The present invention relates to a formulation for and a method of enhancing or increasing the essential oil content in aromatic plants and other plants. It is an object to provide a chemical formulation and a method of applying the chemical formulation to aromatic plants in order to derive significant improvement in the content of essential oil in aromatic crops.

It is a further object of the present invention to provide a method of increasing the essential oil content in an aromatic plant wherein the growth of the plant is not negatively affected when the plant is sprayed or treated with the formulation at the onset of the plant's maturity. Furthermore, the present invention seeks to provide a formulation and a method of treating aromatic plants with such a formulation in order to provide an environmentally safe method of increasing the essential oil content of aromatic plants or crops. The formulation described herein, as well as the method of treatment are environmentally safe in that the formulation comprises amino acids and are applied to the aromatic crops at low concentrations.

It is an object of the present invention to provide a chemical formulation, wherein the formulation comprises an amino acid (such as an isomer of amino butyric acid) and a carrier, and wherein the formulation may further comprise secondary metabolites. The formulation or the elicitor is capable of increasing the synthesis and accumulation of essential oil (which comprises a pool of secondary metabolites) in aromatic crops. Examples of aromatic crops to be used in the present invention include, but are not limited to, rose-scented geranium (*Pelargonium graveolens*) and menthol mint (*Mentha arvensis*). The present invention also provides for a method of increasing the synthesis and accumulation of essential oil in aromatic crops.

DETAILED DESCRIPTION OF THE INVENTION

Accordingly, the present invention provides a formulation which is useful for increasing, in vivo, the synthesis and accumulation of essential oil in aromatic plants. The formulation used as an elicitor comprises an effective amount of a resistance inducer, such as an isomer of amino butyric acid or another amino acid. The formulation may further comprise secondary metabolites as well as a carrier.

In certain embodiments of the present invention, the resistance inducer used in the elicitor formulation may be one of the following: isonicotinamide; DL-2 amino butyric acid; 4-chloro salicylic acid; 2-amino isobutyric acid; o-acetyl salicylic acid; amino salicylic acid; salicylic acid; and 5-nitrosalicylic acid. In certain preferred embodiments of the present invention, the formulation comprises an effective amount of a non-protein DL-2 amino butyric acid. For example, in certain preferred embodiments, the formulation comprises DL-2 amino butyric acid at a concentration of from about 0.1 mM to about 4 mM in water.

The method of using the formulation of the present invention involves applying the formulation to an aromatic crop. For example, single or multiple doses of a solution of DL-2 amino butyric acid having a concentration of from about 0.1 mM to about 4 mM may be sprayed on aromatic crops such as menthol mint (*Mentha arvensis*) and rose-scented geranium (*Pelargonium graveolens*).

The application of the formulation to aromatic plants may occur at various stages within the growth or development of such aromatic plants. For example, in certain embodiments, a solution of DL-2 amino butyric acid may be applied 15 days prior to the harvesting of 100-day-old aromatic plants.

As stated earlier, the formulation comprising a solution of amino butyric acid or another amino acid may further comprise secondary metabolites. Such secondary metabolites may include alkaloids, fatty acids, proteins, and vitamins.

Many varieties of aromatic plants may be treated with the formulation disclosed in the present invention. Examples of aromatic plants which may be used include, but are not limited to, rose-scented geranium (*Pelargonium graveolens*); menthol mint (*Mentha arvensis*); *Chamomilla recutita*; *Artemisia pallens*; *Cymbopogon winterianus*; and the like. In certain preferred embodiments, the aromatic plants employed are *Mentha arvensis* and *Pelargonium graveolens* because of their oil-yielding capacity. Furthermore, the process of applying the formulation to a plant in order to enhance the plant's essential oil content may employ medicinal plants, oilseed crops, pulses, and food crops.

In certain embodiments of the present invention, the essential oil content of the aromatic plants treated by the formulation of the present invention is increased by about 20% to about 46%. For example, when *Pelargonium graveolens* is sprayed with a solution of DL-2 amino butyric acid, its essential oil content is increased by about 46%. Similarly, when *Mentha arvensis* is sprayed with a solution of DL-2 amino butyric acid, its essential oil content is increased by about 27%. The working examples described later in the application illustrate these and other findings.

The present invention also provides for a method of increasing the essential oil content in aromatic plants and other plants. In the present method, certain resistance inducers are first tested to determine whether or not they improve growth in the selected aromatic plants. A resistance inducer, such as an isomer of amino butyric acid or another amino acid, is then selected and included in a formulation. The formulation comprises a solution of the resistance inducer as well as a carrier and/or secondary metabolites.

Subsequently, an aromatic plant is selected, possibly based on its overall growth and yield of essential oil. The selected aromatic plant is then treated with secondary metabolites. The optimal concentration of the resistance inducer in the formulation is then determined, and the formulation (for example, a solution of DL-2 amino butyric acid) is applied to the aromatic plants. In certain embodiments of the present method, the resistance inducer used is an amino butyric acid or another amino acid, for example, isonicotinamide, DL-2 amino butyric acid, 4-chloro salicylic acid, 2-amino isobutyric acid, o-acetyl salicylic acid, amino salicylic acid, salicylic acid, or 5-nitrosalicylic acid.

In the present method, the aromatic plants may be treated with secondary metabolites, such as alkaloids, fatty acids, proteins, and vitamins. Aromatic plants whose essential oil content may be increased by the present method include, but are not limited to, rose-scented geranium (*Pelargonium graveolens*), menthol mint (*Mentha arvensis*), *Chamomilla recutita*, *Artemisia pallens*, and *Cymbopogon winterianus*. Aromatic plants such as *Mentha arvensis* and *Pelargonium graveolens* are used in certain preferred embodiments of the present invention because of their high capacity for yielding essential oil. Furthermore, in other embodiments of the present method, medicinal plants, oilseed crops, pulses, and food crops are treated the formulation according to the present invention.

The following examples are intended to illustrate the invention and should not be construed as limiting the invention in any way.

EXAMPLES

Example 1

Screening of Various Compounds Under Glasshouse Conditions

In this example, fifteen chemicals known to induce resistance in plants were screened by applying the chemicals to four varieties of aromatic plants in pots. The four aromatic plants used in this screening included: *Chamomilla recutita*, *Artemisia pallens*, *Pelargonium graveolens*, and *Mentha arvensis*. Eight chemicals were found to be particularly effective in improving growth and herbage and/or essential oil content. These eight chemicals include isonicotinamide, DL-2 amino butyric acid, 4-chlorosalicylic acid, 2-amino isobutyric acid, o-acetyl salicylic acid, amino salicylic acid, salicylic acid, and 5-nitrosalicylic acid.

Example 2

Field Testing of Identified Compounds

The eight chemicals selected in the previous example for their effects on aromatic plants were subsequently field tested using 2 mM solutions of each chemical in sterilized distilled water. The field tests were performed on *Pelargonium graveolens* cv. Bipuli and *Mentha arvensis* cv. Kosi planted in rows in a randomized block design with three replications, each row constituting a replication, in order to identify the most effective chemicals capable of increasing the essential oil content of the plants. The plants were sprayed with the 2 mM solutions of the chemicals at the onset of maturity, 15 days before harvest. Plants sprayed with sterilized distilled water served as a control group. The results of these field tests are shown in Table 1 below:

TABLE 1

| | | Content of Essential Oil (%) | |
|---|---|---|---|
| Spray No. | Resistance Inducer Used in Spray (2 mM Concentration) | *Pelargonium graveolens* cv. Bipuli | *Mentha arvensis* cv. Kosi |
| 1 | isonicotinamide | 0.14 | 0.70 |
| 2 | DL-2 amino butyric acid | 0.19 | 0.84 |
| 3 | 4-chloro salicylic acid | 0.13 | 0.68 |
| 4 | 2-amino isobutyric acid | 0.12 | 0.72 |
| 5 | o-acetyl salicylic acid | 0.12 | 0.71 |
| 6 | amino salicylic acid | 0.13 | 0.68 |
| 7 | salicylic acid | 0.11 | 0.70 |
| 8 | 5-nitrosalicylic acid | 0.13 | 0.73 |
| 9 | water | 0.13 | 0.66 |
| | LSD (p = 0.05) | 0.01 | 0.06 |

The results in Table 1 above show that application of the DL-2 amino butyric acid solution exhibited the maximum increase (about 46% for *Pelargonium graveolens* cv. Bipuli and about 27% for *Mentha arvensis* cv. Kosi) in essential oil content for the two aromatic plants tested. Application of the isonicotinamide solution resulted in a slight increase in essential oil content, while a slight reduction was observed with salicylic acid and other solutions.

Example 3
Determining the Optimal Crop Maturity Stage for Chemical Application In this example, three of the chemicals described above were further investigated to determine the optimal crop maturity stage for applying the formulation. The three chemicals used in this example were DL-2 amino butyric acid, isonicotinamide, and salicylic acid, all at concentrations of 2 mM. The solutions were tested on *Mentha arvensis* cv. Kosi planted in a randomized block design with 5 replications. In these experiments, the crops were sprayed at 4 different stages of growth and development including 10-day-old crops, 50-day-old crops, 80-day-old crops, and 100-day-old crops. The results of these tests are shown in Table 2 below:

TABLE 2

| Spray No. | Resistance Inducer Used in Spray (2 mM Concentration) | Age of the Crop at the Time of Spray (Days) | Content of Essential Oil (%) |
|---|---|---|---|
| 1 | isonicotinamide | 10 | 0.71 |
|   |   | 50 | 0.70 |
|   |   | 80 | 0.70 |
|   |   | 100 | 0.70 |
| 2 | DL-2 amino butyric acid | 10 | 0.80 |
|   |   | 50 | 0.82 |
|   |   | 80 | 0.81 |
|   |   | 100 | 0.84 |
| 3 | salicylic acid | 10 | 0.70 |
|   |   | 50 | 0.68 |
|   |   | 80 | 0.70 |
|   |   | 100 | 0.70 |
| 4 | water | 10 | 0.67 |
|   |   | 50 | 0.67 |
|   |   | 80 | 0.68 |
|   |   | 100 | 0.66 |
| LSD ($p = 0.05$) |   |   | 0.07 |

The above results illustrate that applying the formulation which comprised DL-2 amino bytric acid served to significantly increase the essential oil content of the crops. The essential oil content increases for the *Mentha arvensis* samples were from about a 19% increase to about a 27% increase, with the maximum increase occurring when the spray was applied to samples of 100-day-old crop (which corresponds to 15 days before harvesting).

Example 4
Large Scale Testing of Selected Compounds

In the present example, field experiments were conducted, wherein 6 larger plots of *Pelargonium graveolens* cv. Bipuli (about 25 m$^2$) were sprayed with solutions of DL-2 amino butyric acid at several different concentrations. An equal number of plots sprayed with sterilized distilled water served as a control group. At least 20 samples of herbage from the sprayed plots and at least 20 samples of herbage from the control plots were distilled in Clevenger type glass apparatus 15 days after spray. The results of these experiments are shown in Table 3 below:

TABLE 3

| Spray No. | Concentration of DL-2 amino butyric acid solution (mM) | Content of Essential Oil (%) |
|---|---|---|
| 1 | 0.1 | 0.16 |
| 2 | 1.0 | 0.17 |
| 3 | 2.0 | 0.20 |
| 4 | 4.0 | 0.20 |
| 5 | 0.0 water | 0.16 |
| LSD ($p = 0.05$) |   | 0.01 |

The results above show an increase in essential oil content of about 25% in *Pelargonium graveolens* where the concentration of DL-2 amino butyric acid was 2 mM and 4 mM.

Further field testing involved samples of herbage of both *Pelargonium graveolens* cv. Bipuli and *Mentha arvensis* cv. Kosi being treated with a solution of DL-2 amino butyric acid at a concentration of about 206 mg/L in water. Similarly to the above tests, large plots were sprayed with the DL-2 amino butyric acid solution, and samples of herbage from both the sprayed plots and the control plots were examined for their essential oil content. The results are summarized in Table 4 below.

TABLE 4

| | | Content of Essential Oil (Mean % ± S.E.) | |
|---|---|---|---|
| Spray No. | Treatment | *Mentha arvensis* | *Pelargonium graveolens* |
| 1 | Sprayed with water | 0.74* ± 0.02 | 0.14 ± 0.01 |
| 2 | Sprayed with DL-2 amino butyric acid | 0.89 ± 0.02 | 0.19 ± 0.01 |

*$n \geq 20$ (where n = number of herbage samples tested)

The results above show an increase in essential oil content of about 20% in *Mentha arvensis* and about 36% in *Pelargonium graveolens* when compared to the herbage samples treated only with water. Further studies of the samples used in these tests showed that the application of DL-2 amino butyric acid did not affect the menthol content in *Mentha arvensis* or the geraniol or citronellol content in *Pelargonium graveolens*.

We claim:

1. A method of increasing the essential oil content in aromatic plants and other plants, said method comprising:
   selecting a resistance inducer, wherein said resistance inducer is capable of improving growth and improving essential oil content in said plants, wherein said resistance inducer is selected from the group consisting of an amino butyric acid, a derivative of an amino butyric acid, isonicotinamide, a derivative of isonicotinamide, a salicylic acid and a derivative of a salicylic acid;
   preparing a formulation comprising said resistance inducer, a carrier, and optionally further comprising secondary metabolites;
   treating said plants with secondary metabolites;
   applying said formulation to said plants; and
   evaluating said plants for an increase in essential oil content.

2. The method of claim 1, wherein said resistance inducer is a non-protein DL-2 amino butyric acid, in an optimum concentration.

3. The method of claim 1, wherein single or multiple doses of said formulation are sprayed on said plants and wherein said formulation comprises said resistance inducer at a concentration of from about 0.1 mM to about 4 mM.

4. The method of claim 3, wherein said formulation comprises DL-2 amino butyric acid at a concentration of from about 0.1 mM to about 4 mM, and wherein single or multiple doses of said formulation are sprayed on said plants.

5. The method of claim 4, wherein said formulation comprising said DL-2 amino butyric acid is sprayed on said plants 15 days prior to the harvesting of 100-day-old plants.

6. The method of claim 1, wherein said formulation comprises secondary metabolites, and wherein said secondary metabolites are selected from the group consisting of alkaloids, fatty acids, proteins, and vitamins.

7. The method of claim 1, wherein said aromatic plants are selected from the group consisting of rose-scented geranium (*Pelargonium graveolens*), menthol mint (*Mentha arvensis*), *Chamomilla recutita*, *Artemisia pallens*, and *Cymbopogon winterianus*.

8. The method of claim 1, wherein said aromatic plants are rose-scented geranium (*Pelargonium graveolens*) or menthol mint (*Mentha arvensis*), said rose-scented geranium (*Pelargonium graveolens*) and menthol mint (*Mentha arvensis*) having an enhanced oil-yielding capacity.

9. The method of claim 1, wherein said other plants are selected from the group consisting of medicinal plants, oilseed crops, pulses, and food crops.

10. The method of claim 1, wherein said essential oil content in said aromatic plants is increased in an amount of from about 20% to about 46%.

11. The method of claim 1, wherein said formulation comprises DL-2 amino butyric acid, wherein said aromatic plant is *Pelargonium graveolens*, and wherein said essential oil content in said *Pelargonium graveolens* is increased by about 46% after application of said formulation.

12. The method of claim 1, wherein said formulation comprises DL-2 amino butyric acid, wherein said aromatic plant is *Mentha arvensis*, and wherein said essential oil content in said *Mentha arvensis* is increased by about 27% after application of said formulation.

13. The method of claim 1, wherein said resistance inducer is isonicotinamide or derivatives thereof.

14. The method of claim 1, wherein said derivative of salicyclic acid is selected from the group consisting of 4-chloro salicylic acid, o-Acetyl salicylic acid, amino salicylic acid, and 5-nitrosalicylic acid.

15. The method of claim 1, wherein said derivative of amino butyric acid is selected from the group consisting of DL-2 amino butyric acid and 2-amino isobutyric acid.

* * * * *

UNITED STATES PATENT AND TRADEMARK OFFICE
CERTIFICATE OF CORRECTION

PATENT NO. : 6,720,289 B2
DATED : April 13, 2004
INVENTOR(S) : Kalra, Alok et al.

It is certified that error appears in the above-identified patent and that said Letters Patent is hereby corrected as shown below:

Column 5,
Line 39, "amino bytric" should read -- amino butyric --

Column 8,
Line 16, "salicyclic acid" should read -- salicylic acid --

Signed and Sealed this

Eighth Day of February, 2005

JON W. DUDAS
*Director of the United States Patent and Trademark Office*